United States Patent [19]

Rogers et al.

[11] 4,312,867
[45] Jan. 26, 1982

[54] ANTIBACTERIAL COMPOUNDS, PROCESSES FOR THEIR PREPARATION AND COMPOSITIONS CONTAINING THEM

[75] Inventors: Norman H. Rogers, Rudgwick; Peter J. O'Hanlon, Redhill, both of England

[73] Assignee: Beecham Group Limited, England

[21] Appl. No.: 190,461

[22] Filed: Sep. 24, 1980

[30] Foreign Application Priority Data

Sep. 28, 1979 [GB] United Kingdom ............... 33720/79

[51] Int. Cl.³ .................... A61K 27/00; A61K 31/35; C07D 309/06
[52] U.S. Cl. ........................... 424/248.5; 260/345.8 R; 542/416; 542/426; 542/427; 424/267; 424/274; 424/283
[58] Field of Search ................. 260/345.8 R; 542/426, 542/427, 416; 424/283, 248.5, 267, 274

[56] References Cited

U.S. PATENT DOCUMENTS 4,102,904 7/1978 Luk et al. ...................... 260/345.8 R

Primary Examiner—Nicky Chan
Attorney, Agent, or Firm—Jacobs & Jacobs

[57] ABSTRACT

Compounds of formula (II):

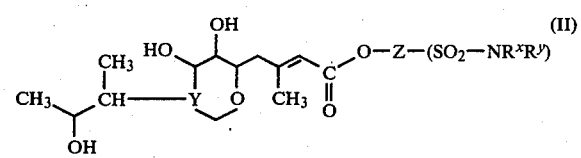

wherein Y is

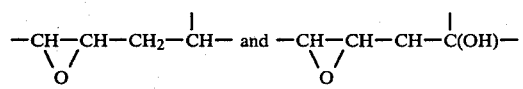

Z represents a divalent radical derived from a $C_{1-20}$ alkane, $C_{3-8}$ cycloalkane, $C_{2-20}$ alkene, arene, aralkane, cycloalkylalkane, heterocycle, or heterocylylalkane; and $R^x$ and $R^y$ are the same or different and each represent (a) hydrogen, or (b) $C_{1-20}$ alkyl, $C_{2-8}$ alkenyl, either of which may be optionally substituted with $C_{3-7}$ cycloalkyl, halogen, carboxy, $C_{1-6}$ alkoxycarbonyl, carbamyl, aryl, heterocyclyl, hydroxy, $C_{1-6}$ alkanoyloxy, amino, mono- or di-($C_{1-6}$) alkylamino; or (c) $C_{3-7}$ cycloalkyl optionally substituted with $C_{1-6}$ alkyl; or (d) aryl; or (e) heterocyclyl; or (f) $R^x$ and $R^y$ together with the nitrogen atom to which they are attached represent a $C_{5-7}$ heterocyclic ring, are useful as antibacterial and antimycoplasma agents.

12 Claims, No Drawings

ANTIBACTERIAL COMPOUNDS, PROCESSES FOR THEIR PREPARATION AND COMPOSITIONS CONTAINING THEM

This invention relates to antibacterial compounds and in particular to a class of sulphonamides which have anti-bacterial activity against certain Gram-positive and Gram-negative organisms, and also possess anti-mycoplasmal activity. The compounds are therefore of value in the treatment of human and veterinary infections.

The compounds of formula (I) and salts and esters thereof:

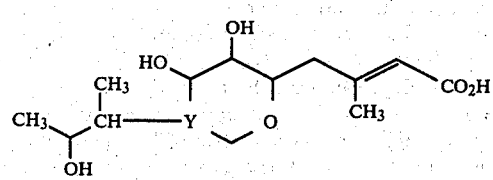

wherein Y represents $-CH=CH-CH_2-\overset{|}{CH}-$, $-\underset{\diagdown\diagup}{CH}-CH-CH_2-\overset{|}{CH}-$ and $-\underset{\diagdown\diagup}{CH}-CH-CH_2-\overset{|}{C}(OH)-$ are disclosed in West German Offenlegungsschriften Nos. 2726619, 2726618 and 2848687 and European Patent Application No. 79300371.6. Compounds of formula (I) having the tri-substituted double bond in the E-configuration are referred to as monic acid C, monic acid A and monic acid B respectively.

The present invention provides a sulphonamide of formula (II);

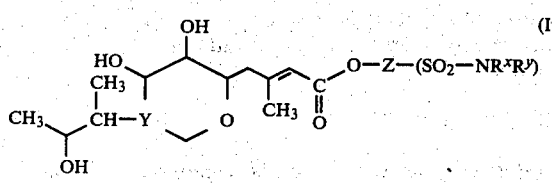

wherein

Y is as defined with respect to formula (I);

Z represents a divalent radical derived from a $C_{1-20}$ alkane, $C_{3-8}$ cycloalkane, $C_{2-20}$ alkene, arene, aralkane, cycloalkylalkane, heterocycle, or heterocylylalkane; and $R^x$ and $R^y$ are the same or different and each represent (a) hydrogen, or (b) $C_{1-20}$ alkyl, $C_{2-8}$ alkenyl, either of which may be optionally substituted with $C_{3-7}$ cycloalkyl, halogen, carboxy, $C_{1-6}$ alkoxycarbonyl, carbamyl, aryl, heterocyclyl, hydroxy, $C_{1-6}$ alkanoyloxy, amino, mono- or di-($C_{1-6}$) alkylamino; or (c) $C_{3-7}$ cycloalkyl optionally substituted with $C_{1-6}$ alkyl; or (d) aryl; or (e) heterocyclyl; or (f) $R^x$ and $R^y$ together with the nitrogen atom to which they are attached represent a $C_{5-7}$ heterocyclic ring.

The term 'aryl' includes phenyl and naphthyl optionally substituted with up to five halogen, $C_{1-6}$ alkyl, $C_{1-6}$ alkoxy, halo ($C_{1-6}$) alkyl, hydroxy, amino, carboxy, $C_{1-6}$ alkoxycarbonyl, or $C_{1-6}$ alkoxycarbonyl ($C_{1-6}$) alkyl groups.

The term 'heterocyclyl' includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo ($C_{1-6}$) alkyl, hydroxy, amino, carboxy, $C_{1-6}$ alkoxycarbonyl, $C_{1-6}$ alkoxy-carbonyl ($C_{1-6}$) alkyl, aryl or oxo groups.

Preferably the compounds of formula (II) are derivatives of monic acid A, i.e. Y represents

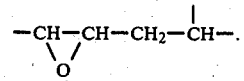

Suitably the group Z represents straight or branch chain $C_{1-10}$ alkylene, $C_{4-6}$ cycloalkylene, phenylmethyl; preferably Z represents straight chain $C_{1-10}$ alkylene or a group

wherein X represents straight chain $C_{1-8}$ alkylene and $R°$ represents methyl or ethyl.

Suitable groups for $R^x$ and $R^y$ include hydrogen and $C_{1-10}$ alkyl, or $R^x$ and $R^y$ together with the nitrogen atom to which they are attached form a pyrrolidinyl, piperidinyl, or morpholinyl ring. Preferably $R^x$ and $R^y$ represent hydrogen; or $C_{1-5}$ alkyl, in particular methyl or ethyl.

Specific compounds of this invention include:
3-sulphamoyl propyl monate A
6-sulphamoyl hexyl monate A
8-sulphamoyl octyl monate A
3-N,N-dimethyl sulphamoyl propyl monate A
7-sulphamoyl-hept-2-yl monate A Compounds of this invention have antibacterial and antimycoplasmal activity, and are, therefore, of value in the treatment of bacterial and mycoplasma-induced human and veterinary diseases.

The infections against which compounds of this invention are particularly useful include venereal disease. They are also effective in the treatment of respiratory infections such as bacterial bronchitis; and bacterial meningitis, non-speciific urethritis and pneumonia. In animals it may be employed for the treatment of mastitis in cattle, for swine dysentery, and for mycoplasmal infections in animals such as turkeys, chickens, pigs and cattle.

Some of the human and veterinary diseases either caused by Mycoplasma species or in which they play a prominent role, and against which compounds of this invention are effective, are as follows:

| | |
|---|---|
| Avian | |
| M. gallisepticum | Chronic respiratory diseases (airsacculitis) of chickens and turkeys. |
| M. synoviae | Airsacculitis and infectious synovitis |
| Bovine | |
| M. bovis | Mastitis, respiratory disease and arthritis of cattle |
| M. dispar | Calf pneumonia |
| Porcine | |
| M. suipneumoniae | Enzootic pneumonia of pigs |
| M. hyorhinis | } arthritis in pigs |
| M. hyosynoviae | |
| Murine | |
| M. pulmonis | pneumonia of rats and mice |
| M. arthritidis | arthritis in rats and mice |
| Human | |

| | |
|---|---|
| *M. pneumoniae* | primary atypical pneumonia |

Compounds of the present invention are particularly useful in the treatment of enzootic pneumonia in animals such as pigs, cattle and sheep, because they also have activity against the bacteria *Bordetella bronchispetica, Pasteurella multocida* and *Haemophilus spp*, which often cause respiratory complications in cases of this disease.

This invention also provides a pharmaceutical or veterinary composition which comprises a compound of formula (II) together with a pharmaceutically or veterinary acceptable carrier or excipient.

The compositions may be formulated for administration by any route, and would depend on the disease being treated. The compositions may be in the form of tablets, capsules, powders, granules, lozenges, liquid or gel preparations, such as oral, topical or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin compounds of this invention may be made up into a cream, lotion or ointment. Cream or ointment formulations that may be used for compounds of formula (II) are conventional formulations well known in the art, for example, as described in standard text books of pharmaceutics and cosmetics, such as Harry's Cosmeticology published by Leonard Hill Books, and the British Pharmacopoeia.

Suppositories will contain conventional suppository bases, e.g. cocoa-butter or other glyceride.

For parental administration, fluid unit dosage forms are prepared utilizing the compound and a sterile vehicle, water being preferred. The compound, depending on the vehicle and concentration used, can either be suspended or dissolved in the vehicle. In preparing solutions the compound can be dissolved in water for injection and filter sterilized before filling into a suitable vial or ampoule and sealing. Advantageously, adjuvants such as a local anaesthetic, preservative and buffering agents can be dissolved in the vehicle. To enhance the stability the composition can be frozen after filling into the vial and water removed under vacuum. The dry lyophilized powder is then sealed in the vial. Parental suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compounds.

Veterinary compositions for intrammary treatment of mammary disorders in animals, especially bovine mastitis, will generally contain a suspension of a compound of formula (II) in an oily vehicle.

The compositions may contain from 0.1% to 99% by weight, preferably from 10-60% by weight, of the active material, depending on the method of administration. Where the compositions comprise dosage units, each unit will preferably contain from 50-500 mg, of the active ingredient. The dosage as employed for adult human treatment will preferably range from 100 mg to 3 g, per day, for instance 250 mg to 2 g, per day, depending on the route and frequency of administration.

Alternatively a compound of formula (II) may be administered as part of the total dietary intake. In this case the amount of compound employed may be less than 1% by weight of the diet and in preferably no more than 0.5% by weight. The diet for animals may consist of normal foodstuffs to which the compound may be added or it may be added to a premix.

A suitable method of administration of a compound of formula (II) to animals is to add it to the animals drinking water. In this case a concentration of compound in the drinking water of about 5–500 µg/ml, for example 5–200 µg/ml, is suitable.

Compounds of formula (II) may be prepared by esterification of a carboxylic acid of formula (I) or a salt or other reactive derivative of the acid with an alcohol of formula (III)

$$HO-Z-SO_2NR^xR^y \qquad (III)$$

an esterifying derivative thereof, wherein $R^x$, $R^y$ and Z are as defined with respect to formula (II).

Some of the alcohols and ester forming derivatives thereof used in the preparation of compounds of formula (II) are known. The following literature reference describe generally applicable methods which may be used to prepare these and other starting materials:

H. G. Houlton and H. V. Tarter, *J. Amer. Chem. Soc.* 1938, 60. 544

B. Helfrich and K. G. Kleb, *Ann.*, 1960, 635, 91

J. P. Stewart and H. P. Cordts, *J. Amer. Chem. Soc.* 1952, 74. 5880

Esterification may be performed by any conventional method, for example by reaction of the free acid with the appropriate alcohol $HO-Z-SO_2-NR^xR^y$ in the presence of a catalyst or by reaction of a salt of the free acid:

(a) with the appropriate halide or sulphate of the alcohol $HO-Z-SO_2-NR^xR^y$ in the presence of dimethylsulphoxide and calcium carbonate or with the halide in the presence of hexamethyl phosphoramide; or (b) by phase transfer catalysis methods with the halide and/or sulphate of the alcohol in aqueous and/or organic solution in the presence of a quaternary ammonium salt such as tetrabutyl ammonium bisulphate or halide, or benzyltrimethylammonium halide.

The formation of compounds (II) wherein Y represents

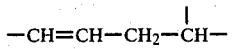

may also by carried out by conventional transesterification methods, for example reaction of a suitable ester of compound (I) with the appropriate alcohol HO—Z—SO$_2$NR$^x$R$^y$ in the presence of a catalyst such as sodium salt of the alcohol, or dry hydrogen chloride, p-toluenesulphonic acid, or potassium cyanide.

Alternatively, the mixed anhydride derivative of the acid (I) may be reacted with an alcohol HO—Z—SO$_2$NR$^x$R$^y$, or alkali metal or alkaline earth metal alkoxide such as the lithium, sodium or magnesium alkoxide. Suitable mixed anhydrides are alkoxyformic anhydrides, or anhydrides with, for example trimethyl acetic acid, thioacetic acid, diphenylacetic acid, benzoic acid, phosphorus acids (such as phosphoric or phosphorous acids), sulphuric acid or aliphatic or aromatic sulphonic acids (such as p-toluenesulphonic acid). The mixed anhydride may be generated in situ, for example, using isobutyl chloroformate or ethyl chloroformate.

The compound of the present invention also may be prepared from the intermediate ketone of formula (IV) by any method known to convert a ketone into an α,β-unsaturated ester. One such process comprises reacting a compound of formula (IV), wherein Y represents

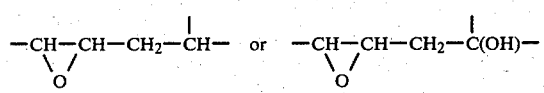

and in which the hydroxyl groups may be protected, with a compound of formula (V) or (VI):

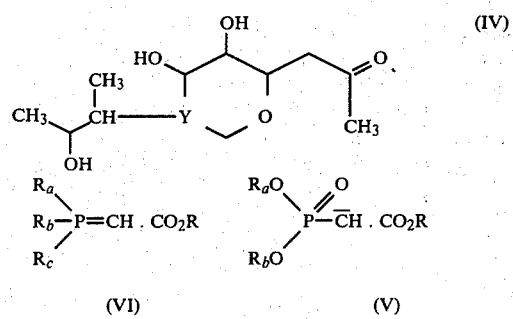

in which formulae (V) and (VI) the symbols R$_a$, R$_b$ and R$_c$ are the same or different and each is lower alkyl, aryl or aralkyl, and R is a group Z—SO$_2$—NR$^x$R$^y$ as defined with respect to formula (II) above; and subsequent removing any hydroxyl protecting groups.

The preferred embodiment of this process comprises reacting compound (IV) with compound (V). Preferably, in this case R$_a$ and R$_b$ are methyl or ethyl. In the case when compound (IV) is reacted with compound (VI), then R$_a$, R$_b$ and R$_c$ are preferably all phenyl.

The reaction is usually carried out in an inert solvent such as dimethylformamide, hexane, benzene, tetrahydrofuran for example, at a temperature of from about 10° C. to about 100° C. preferably under an inert gas such as nitrogen. Under these conditions the reaction proceeds smoothly over a period of from a few minutes to a few hours and the product may be isolated by any of the usual techniques, e.g. solvent evaporation or anti-solvent precipitation followed by filtration. In many cases the reaction may be carried out in a solvent in which the product is insolublle and in such cases the precipitation solid may be collected by filtration. Purification of the product may be by any of the usual chromatographic or recrystallisation techniques.

Compounds of formula (II) wherein Y represents

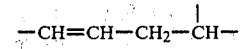

may be prepared from compounds of formula (II) wherein Y represents $$-CH-CH-CH_2-CH- \text{ by}$$
$$\diagdown O \diagup$$

reaction with a reagent which converts as epoxide to an olefin.

A number of reagents for converting an epoxide to an olefin are known in the literature, and the particular reagent of choice for the process of the present invention is a matter of trial and error. Some such reagents are more suitable than others for this purpose. Some generally applicable methods are as follows:

(a) Potassium selenocyanate in methanol/water; (see JCS Perkin I, 1975, 1216)

(b) Lower valent tungsten halides; for example WCl$_6$/butyl lithium (see J. Amer. Chem. Soc. 1972, 94, 6538)

(c) Ph$_3$P=Se/trifluoroacetic acid; (see JCS Chem. Comm. 1973, 253)

(d) Trifluoroacetyl iodide/sodium iodide; (see. J. Org. Chem., 1978, 43, 1841).

Other methods are described in the following references:

J. Amer. Chem. Soc., 1973, 95, 2687.
Tet: Letts (17) 1976, 1395.
Ber. 1955, 88, 1654.
J. Org. Chem., 1957, 22, 1118.

It has been found that one convenient method is the use of potassium selenocyanate.

Suitable solvents for use with potassium selenoxyanate include mixtures of water with alkanols, in particular C$_1$-C$_{20}$ alkanols. It has been found that higher yields of the compound of formula (II) are achieved if an alcohol is employed with a large, in particular branched or cyclic, alkyl group. Specific alcohols include isohexyl alcohol, tert-amyl alcohol and cyclohexyl alcohol. The reaction is generally performed at elevated temperatures, suitably at about the boiling point of the solvent employed. The time for which the reaction is performed depends on the temperature of the reaction, and therefore on the solvent. Generally a time of from 1-9 days is suitable.

Another suitable method for converting an epoxide into an olefin, comprises treatment with trifluoroacetyl iodide and sodium iodide. The trifluoroacetyl iodide may be prepared in situ from trifluoroacetic anhydride. The reaction is suitably conducted at ambient temperatures for from about 10 to 36 hours, suitably about 24 hours.

Prior to the above processes of this invention, it may be desirable to protect the hydroxyl groups in compounds of formulae (I) and (IV). Although reaction is possible without hydroxyl protection, in some cases higher yields could be formed if the hydroxyl groups were protected. Such protecting groups must be removable under suitably mild conditions and suitable groups include silyl groups produced from a silylating agent as discussed above. Particularly suitable hydroxyl-protecting groups include tri-methylsilyl, t-butyldimethylsilyl, methylthiomethyl. A preferred hydroxyl-protecting group is trimethylsilyl, as it is readily removed on completion of the reaction. Alternatively, for some reactions it is possible to protect the hydroxyl groups with other ester radicals which may be removed by chemical or enzymatic means. Examples include p-nitrobenzoate, methoxyacetate, phenoxyacetate, trifluoroacetate, each of which may be removed under mild basic conditions such as aqueous ammonia; or potassium carbonate in aqueous methanol.

It is also possible to protect the glycol moiety in compounds of formula (I) and suitable reagents for forming such a hydroxyl-protecting group include compounds of formula (VII).

(VII)

wherein $R^1$ is hydrogen or a $C_{1-6}$ alkyl group and $R^2$, $R^3$ and $R^4$ independently represent a $C_{1-6}$ alkyl group.

The group $R^1$ may be for example hydrogen, methyl, ethyl, n- or iso-propyl. Most suitably, $R^1$ represents hydrogen so that the compound of formula (VII) is a trialkyl orthoformate.

Groups $R^2$, $R^3$ and $R^4$ may be for example, methyl, ethyl, n- or iso-propyl, n-, iso-, sec- or tert-butyl. Preferably $R^2$, $R^3$ and $R^4$ are all the same and each represents a methyl group.

Other glycol protecting groups include those wherein the glycol moiety is converted to the structure:

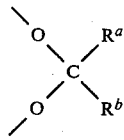

where $R^a$ and $R^b$ are hydrogen, $C_{1-6}$ alkyl, or phenyl. Preferably $R^a$ and $R^b$ are both methyl, i.e. the group is the isopropylidene group. This group may be introduced by reaction with 2,2-dimethoxypropane, and removed by treatment with acetic acid.

The hydroxy-protecting group may be removed by a conventional method for the particular hydroxyl-protecting group.

It may be such that it can be removed directly or alternatively, it may be converted into a different protecting group which is then removable under different conditions. This latter approach may be employed when a glycol protecting group derived from a compound (VII) is used; it is converted by acid to the group —$OCOR^1$ which is then removed.

The following Examples illustrate the preparation of a number of compounds of the present invention.

EXAMPLE 1

3-Sulphamoylpropyl monate A

Sodium monate A (732 mgs) was added to a solution of 3-chloropropanesulphonamide (315 mgs) and sodium iodide (300 mgs) in DMF (25 ml). The solution was stirred overnight at room temperature then heated at 80° C. for ca. 18 hours then evaporated to an oil. This was extracted with ethylacetate (25 ml)-brine (25 ml) and the organic phase washed with brine then dried (MgSO$_4$). The solvent was removed in vacuo and the residue chromatographed on silica (8 g) eluting with 0–7% methanol-chloroform. Pure fractions (tlc) were combined and evaporated to yield 3-sulphamoylpropyl monate A, 205 mgs, (22%) $\nu_{max}$ (KBr) 3400 (broad), 1700, 1640, 1450, 1325, 1228 and 1142 cm$^{-1}$; $\nu_{max}$ (EtOH) 220 mm (εm 13 000); $\delta_H$(CD$_3$OD) 0.93 (3H, d, CH$_3$-17), 1.20 (3H, d, CH$_3$-14), 2.18 (3H, s, CH$_3$-15), 4.20 (3H, t, CO$_2$CH$_2$), 5.76 (1H,s, H-2); δc(CD$_3$OD) 167.8 (C1), 159.6 (C3), 117.8 (C2), 76.0 (C5), 71.4 (C13), 70.6 (C7), 69.9 (C6), 66.2 (C16), 62.7 (C3'), 61.3 (C11), 56.8 (C10), 52.8 (C1'), 43.8 (C4), 43.5 (C12), 41.3 (C8), 32.8 (C9), 24.8 (C2'), 26.3 (C14), 19.4 (C15), 12.2 (C17) (Found: 447.1927. M$^+$-H$_2$O requires 447.1928).

EXAMPLE 2

6-Sulphamoylhexyl monate A

Sodium monate A (0.732 g) was added to a solution of 6-chlorohexane sulphonamide (400 mgs) and sodium iodide (300 mgs) in DMF (25 ml). The reaction was stirred at 70° C. overnight then the solvent removed in vacuo. The residue was dissolved in ethyl acetate (25 ml)-brine (25 ml) and the organic phase separated, washed with brine (25 ml) then dried (MgSO$_4$). After evaporation of the solvent the crude product was chromatographed on silica (15 g) eluting with 0–8% methanolchloroform. Fractions containing pure product (tlc) were combined and evaporated to dryness to give 6-sulphamoylhexyl monate A, 320 mgs, (32%) $\nu_{max}$ (CHCl$_3$) 3400 (broad), 1700, 1640, 1510 and 1415 cm$^{-1}$; $\nu_{max}$ (EtOH) 219 nm (εm 13,200); $\delta_H$(CD$_3$OD) 0.94 (3H, d, CH$_3$-17), 1.17 (3H, d, CH$_3$-14), 1.48 (8H, m, CH$_2$(CH$_2$)$_4$CH$_2$), 2.17 (3H, s, CH$_3$-15), 4.07 (2H, t, CO$_2$CH$_2$), 5.74 (1H, s, H-2); δc (CD$_3$OD) 168.0 (C1), 158.8 (C3), 118.1 (C2), 75.9 (C5), 71.3 (C13), 70.6 (C7), 69.8 (C6), 66.1 (C16), 64.6 (C10), 55.6 (C11), 43.7 (C4), 43.4 (C12), 41.2 (C8), 32.7 (C9), 29.3 (C9), 29.3 (C5'), 28.7 (C3'), 26.4 (C4'), 24.7 (C2'), 20.3 (C14), 19.3 (C15), 12.2 (C17).

EXAMPLE 3

8-Sulphamoyloctyl monate A

8-Chloro-octyl sulphonamide (455 mgs) was added to a solution of sodium monate A (732 mgs) and sodium iodide (300 mgs) in DMF (30 ml). The reaction was stirred at 80° C. overnight then the solvent evaporated in vacuo. The residue was dissolved in ethyl acetate (20 ml)-brine (20 ml) and the organic phase separated, washed with brine and dried (MgSO$_4$). After removal of the solvent in vacuo, the crude product was chromatographed on silica (10 g) eluting with 0–8% methanol-chloroform. The fractions containing pure product were combined and evaporated to give 8-sulphamoyloctyl monate A, 482 mgs (45%) $\nu_{max}$ (KBr) 3400, 1700, 1641, 1542, 1327, 1225 and 1145 cm$^{-1}$; $\nu_{max}$ (EtOH) 219 nm ($\epsilon$m 13,900); $\delta_H$(CH$_3$OD) 0.92 (3H, d, CH$_3$-17), 1.17 (3H, d, CH$_3$-14), 1.35 (12H, m (CH$_2$)$_6$), 2.17 (3H, d, CH$_3$-15), 5.73 (1H, broad, s, H-2); $\delta_C$(CD$_3$OD) 167.7 (C1), 158.4 (C3), 117.8 (C2), 75.8 (C5), 71.0 (C13), 70.3 (C7), 69.5 (C6) 65.8 (C16), 64.3 (C8'), 61.0 (C11), 56.3 (C10), 55.5 (C1'), 43.4 (C4), 43.1 (C12), 40.8 (C8), 32.3 (C9), 29.5 (C4',5'), 29.2 (C7'), 28.7 (C3'), 26.5 (C6'), 24.4 (C2'), 20.3 (C14), 19.2 (C15), 12.1 (C17).

EXAMPLE 4

3-N,N-Dimethylsulphamoylpropyl monate A

3-Chloro-N,N-dimethylpropanesulphonamide (653 mgs) was added to a solution of sodium monate A (1.1 g) in DMF (30 ml) and sodium iodide (0.45 g). The reaction was stirred at 80° C. overnight, then the solvent removed in vacuo and the residue dissolved in ethyl acetate brine. The organic phase was washed with saturated sodium bicarbonate and brine then dried (over magnesium sulphate). After removal of the solvent, the product was chromatographed on silica (10 g) eluting with 2-6% methanol in chloroform. Fractions containing pure product were evaporated to give 3-N,N-dimethylsulphamoylpropyl monate A 390 mgs, (25%) m.p. 130°-2° C., $\nu_{max}$ 3470, 3350, 1728 and 1645 cm$^{-1}$; $\nu_{max}$ (EtOH) 224 nm ($\epsilon$13,919); $\delta_H$ (CD$_3$OD) 0.92 (3H, d, CH$_3$-17), 1.21 (3H, d, CH$_3$-14), 2.15 (3H, s, CH$_3$-15) 2.82 (6H, s, N(CH$_3$)$_2$), 4.18 (2H, t, CH$_2$-1'), 5.73 (1H, s, H-2); $\delta_C$(CDCl$_3$/CD$_3$OD) 167.3 (C1), 159.3 (C3), 117.4 (C2), 75.6 (C5), 71.0 (C7), 70.4 (13), 69.4 (C6), 66.0 (C16), 62.2 (C1'), 61.0 (C11), 56.3 (C10), 49.0 (C3'), 43.6 (C4), 43.1 (C12), 40.8 (C8), 37.6 (N(CH$_3$)$_2$), 32.4 (C9), 23.6 (C2') 20.2 (C14), 19.3 (C15), 12.1 (C17); m/e (relative intensity) 493 (M+0.5%), 455 (1), 457 (1), 431 (2), 227 (46), 111 (100) (Found: 493.2335. C$_{22}$H$_{39}$NO$_9$S requires 493.2325).

EXAMPLE 5

7-Sulphamoylhept-2-yl monate A

Sodium monate A (1.1 g) was added to a solution of 6-chloroheptane-sulphonamide (0.64 g) and sodium iodide (0.45 g) in DMF (30 ml) and the reaction heated at 80° C. overnight. After evaporation of the solvent in vacuo the residue was extracted with ethyl acetate/brine and the organic phase washed with sodium bicarbonate and brine then dried (over magnesium sulphate). The ethyl acetate was evaporated under reduced pressure and the product chromatographed on silica (10 g) eluting with 0-8% methanol in chloroform. Fractions containing pure product (tlc) were combined and evaporated to give 7-sulphamoylhept-2-yl monate A 181 mgs, (12%) $\nu_{max}$ (film) 3400 (broad), 1700, 1642, 1325 and 1145 cm$^{-1}$; $\mu_{max}$ (EtOH) 222 nm ($\epsilon$11,985); $\delta_H$ (CD$_3$OD) 0.95 (3H, d, CH$_3$-17), 1.11 (6H, dd, CH$_3$-14, CH$_3$-1'), 1.18 (3H, s, CH$_3$-15), 5.78 (1H, s, H-2), $\delta_C$ (CD$_3$OD) 168.3, 168.0 (C1), 159.2, 158.9 (C3), 118.3 (C2), 76.2 (C5), 71.6 (C13), 70.7 (C7), 70.0 (C6), 66.4 (C16), 64.6 (C6'), 61.4 (C11), 56.8 (C10), 55.8 (C1'), 43.9 (C12), 43.7 (C4), 41.5 (C8), 32.9 (C9), 29.5, 28.9, 26.6 (C2', 3', 4', 5'), 24.9 (C7'), 20.4 (C14), 19.3 (C15), 12.3 (C17); m/e (relative intensity) 507 (0.5%), 489 (1.5), 445 (2), 227 (78), 101 (100) (Found 489.2359. M+-CH$_3$OH C$_{23}$H$_{39}$NO$_8$S requires 489.2359).

BIOLOGICAL DATA

(a) Human Bacteria

Table 1 shows the MIC values ($\mu$g/ml) of the compounds of Examples 1 to 3 against a number of organisms important in human infections obtained by serial dilution in nutrient agar containing 5% 'chocolated' horse blood.

(b) Veterinary Bacteria

Table 2 shows the MIC values ($\mu$g/ml) of the compounds of the Examples against a number of organisms important in veterinary infections obtained by serial dilution in agar (diagnostic sensitivity test agar).

(c) Anti-Mycoplasmal Activity

Table 3 shows the in vitro MIC values ($\mu$g/ml) of the compounds of Examples 1 to 3 against a number of mycoplasma organisms. The minimum inhibitory concentrations (MIC) of the examples were determined by either:

(i) in Friis' broth using microtitre plates, by modification of the metabolic-inhibition test (Taylor-Robinson, Post Frad, Med. J., 1967, 43, 100).

or (ii) by serial dilution in Friis' agar medium.

TABLE 1

| ORGANISM | Compound of Example Number | | | | |
|---|---|---|---|---|---|
| | 1 | 2 | 3 | 4 | 5 |
| E. coli NCTC 10418 | >100 | >100 | >100 | >100 | >100 |
| E. coli ESS | 25 | 0.5 | 0.5 | 2.5 | 2.5 |
| P. mirabilis 889 | 100 | 50 | >100 | >100 | >100 |
| K. aerogenes A | >100 | >100 | >100 | >100 | >100 |
| Ps. aeruginosa 10662 | >100 | >100 | >100 | >100 | >100 |
| Pasteurella multocida 1633 | 0.5 | 2.5 | 1.0 | 0.5 | 2.5 |
| Haemophilus influenzae Q1 | 0.05 | 0.1 | 0.2 | 0.1 | 0.2 |
| Haemophilus influenzae Wy21 | 0.05 | — | 0.2 | 0.1 | 0.2 |
| Neisseria catarrhalis 1502 | — | — | 1.0 | 1.0 | 1.0 |
| Bacillus subtilis 6633 | 10 | 0.5 | 0.2 | 2.5 | 2.5 |
| Corynebacterium xerosis 9755 | >100 | >100 | >100 | No Growth | No Growth |
| Sarcina lutea 8340 | >100 | >100 | >100 | No Growth | No Growth |
| Staph aureus Oxford | 50 | 5.0 | 1.0 | 10 | 10 |
| Staph aureus Russell | 50 | 5.0 | 1.0 | 10 | 10 |
| Staph aureus W2827 | 100 | 5.0 | 1.0 | 10 | 25 |
| Strep faecalis I | >100 | >100 | >100 | >100 | >100 |
| Strep pyogenes A 64/848 | 0.5 | 0.5 | 0.5 | 2.5 | 2.5 |
| Strep pyogenes B 2788 | 2.5 | 1.0 | 1.0 | 2.5 | 2.5 |
| Strep pyogenes C 2761 | 2.5 | 1.0 | 1.0 | 5.0 | 2.5 |
| Strep pneumoniae CN33 | 0.5 | 0.2 | 0.5 | 1.0 | 1.0 |

TABLE 2

| | Compound of Example Number | | | | |
|---|---|---|---|---|---|
| | 1 | 2 | 3 | 4 | 5 |
| E. coli NCTC 10418 | >80 | >80 | >80 | >80 | >80 |
| E. coli E1 | >80 | >80 | >80 | >80 | >80 |
| S. dublin S7 | >80 | >80 | >80 | >80 | >80 |
| S. typhimurium S18 | >80 | >80 | >80 | >80 | >80 |
| Bord bronchiseptica B08 | 80 | 20 | 80 | 80 | 40 |
| Bord bronchiseptica B09 | 20 | 10 | 40 | 20 | 10 |
| Past multocida PA1 | 0.625 | 0.312 | 1.25 | 0.625 | 0.625 |
| Past multocida PA2 | 0.156 | 0.039 | 0.156 | 0.312 | 0.312 |
| Past haemolytica PA5 | 10 | 5 | 5 | 10 | 5 |
| Erysipelothrix rhusiopathiae NCTC 8163 | >80 | 20 | 10 | >80 | 40 |
| Corynebacterium pyogenes CY1 | >80 | 10 | — | >80 | 80 |
| Staph aureus B4 (pen. resis) | 40 | 2.5 | 0.625 | 5 | 5 |
| Staph aureus 152 (pen. sens) | 20 | 1.25 | 0.625 | 2.5 | 1.25 |
| Staph aureus Oxford | 40 | 2.5 | 0.625 | 2.5 | 1.25 |
| Strep suis (group D) SPS11 | 80 | 2.5 | 20 | 40 | 5 |
| Strep uberis SPU1 | 1.25 | 0.625 | 1.25 | 2.5 | 0.625 |
| Strep dysgalaciae SPD1 | 2.5 | 0.625 | 2.5 | 2.5 | 0.625 |
| Strep agalactiae SPA1 | 2.5 | 1.25 | 2.5 | 2.5 | 1.25 |
| B. subtilis ATCC 6633 | — | — | — | No Growth | No Growth |

TABLE 3

| | Compound of Example No | | | | | |
|---|---|---|---|---|---|---|
| | 1 | | 2 | | 3 | |
| ORGANISM | BROTH | AGAR | BROTH | AGAR | BROTH | AGAR |
| M suipneumoniae Str 11 | 0.078 | | ≦0.02 | | 0.02 | |
| M suipneumoniae J2206/183b | 0.312 | | 0.156 | | 0.156 | |
| M dispar H225 | 0.039 | | <0.02 | | 0.02 | |
| M dispar NCTC 10125 | 0.078 | | <0.02 | | 0.02 | |
| M pneumoniae 427a | 2.5 | 2.5 | 0.312 | 0.312 | 0.312 | 0.312 |
| M pneumoniae ATCC 15492 | 2.5 | 5.0 | 0.312 | 0.625 | 0.312 | 0.625 |
| M bovis ATCC 25025 | | 0.078 | | <0.02 | | 0.02 |
| M bovis NCTC 10131 | | 0.039 | | <0.02 | | 0.02 |
| M fermentans MWKL4 | 0.039 | 0.078 | <0.02 | 0.039 | 0.02 | 0.039 |
| M pulmonis JB | 0.02 | 0.039 | <0.02 | ≦0.02 | 0.02 | 0.039 |
| M hyorhinis ATCC 23234 | | 0.312 | | 0.156 | | 0.312 |
| M hyosynoviae ATCC 25591 | | 0.156 | | 0.039 | | 0.078 |
| M arthritidis ATCC 14124 | | >10 | | 5.0 | | 5.0 |
| M gallisepticum S6 | | >10 | | 2.5 | | 2.5 |
| M synoviae ATCC 25204 | | <0.02 | | <0.02 | | <0.02 |
| M alkalescens NCTC 10135 | | 0.039 | | <0.02 | | <0.02 |
| M bovigenitalium ATCC 14173 | | 0.039 | | ≦0.02 | | <0.039 |

(d) Anti-mycoplasmal Activity

Table 4 shows the in vivo MIC values (mg/ml) of the compounds of Examples 4 and 5 against a number of Mycoplasma organisms. The values were determined in Friis broth solidifed with 0.9% agarose. The inoculum was $10^3$ to $10^5$ CFV and the MIC's were recorded after 6 days incubation at 37° C.

TABLE 4

| ORGANISM | Compound of Example No | |
|---|---|---|
| | 4 | 5 |
| M. suipneumoniae NB12 | 0.5 | 0.5 |
| M. suipneumoniae JF435 | 1.0 | 0.5 |
| M. suipneumoniae HK(2) | 1.0 | 1.0 |
| M. suipneumoniae Str. 11 | 0.5 | 0.25 |
| M. suipneumoniae J2206/183b | 1.0 | 0.5 |
| M. suipneumoniae MS16 | 0.5 | 0.25 |
| M. suipneumoniae PW/C/210 | 0.5 | 0.25 |
| M. suipneumoniae LABER | 0.5 | 0.25 |
| M. suipneumoniae UCD1 | 1.0 | 1.0 |
| M. suipneumoniae TAM 6N | 1.0 | 0.5 |
| M. suipneumoniae ATCC 25095 | 0.5 | 0.25 |
| M. suipneumoniae NCTC 10110 | 1.0 | 0.5 |
| M. hyorhinis ATCC 23234 | 0.25 | 0.25 |
| M. hyorhinis ATCC 25021 | 0.25 | 0.25 |
| M. hyosynoviae ATCC 25591 | 0.25 | 0.1 |
| M. bovis NCTC 10131 | ≦0.01 | ≦0.01 |
| M. bovigenitalium ATCC 14173 | 0.05 | 0.05 |
| M. dispar NCTC 10125 | 0.25 | 0.1 |
| M. gallisepticum S6 | >10.0 | 2.5 |
| M. pneumoniae ATCC 15492 | 5.0 | 1.0 |
| Mean MIC for above 12 strains of M. suipneumoniae | 0.75 | 0.48 |

(e) Serum binding

Serum binding was assessed by ultrafiltration of porcine serum containing compounds at 8 mcg/ml, and through an Amicon CF50A ultrafiltration cone. Separation of ultrafiltrate was achieved by centrifugation. Unbound concentrations of compound were measured in the ultrafiltrate by microbiological assay (B. subtilis ATCC 6633) against standards prepared in saline. Results are given in Table 5.

TABLE 5

| Compound of Example No. | % bound to pig serum. |
|---|---|
| 1 | — |
| 2 | 71.3 |
| 3 | 96.5 |

TABLE 5-continued

| Compound of Example No. | % bound to pig serum. |
|---|---|
| 4 | 94.7 |
| 5 | 64.6 |

(f) Mean serum concentrations in neonatal piglets after intramuscular or oral administration at 50 mg/kg of 6-sulphamoylhexyl monate A Blood levels were assessed in neonatal piglets (2 to 4 animals per group and mean bodyweights about 2 kg). The dose was 50 mg/kg (dose solution=25 mg/ml in 25% ethanol). Doses were given by intramuscular injection and orally by stomach tube. Piglets were bled at intervals up to 6 and at 24 hours, and serum assayed microbiologically (*B. subtilis* ATCC 6633). Results are given in Table 6.

TABLE 6

| Compound of Example No | Route of administration | Serum concentrations (μg/ml) at: | | | | | | | |
|---|---|---|---|---|---|---|---|---|---|
| | | 10' | 20' | 40' | 1h | 2h | 3h | 4h | 5h |
| 2 | i.m. | 31.4 | 31.2 | 23.7 | 17.3 | 9.2 | 3.2 | 1.02 | <0.60 |
| | p.o. | 5.9 | 8.3 | 8.6 | 5.9 | 1.8 | 1.5 | 0.74 | <0.51 |

' represents minutes

We claim:

1. A compound of the formula:

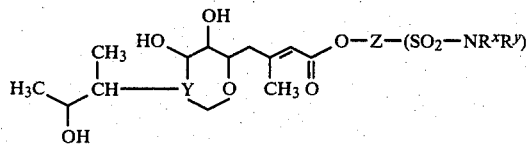

wherein Y is —CH=CHCH$_2$CH $\diagdown$ , —CH—CHCH$_2$CH $\diagdown$ , or
$\qquad\qquad\qquad\qquad\qquad\quad$ \\O/

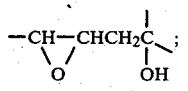

Z is a member selected from the group consisting of alkylene of 1 to 20 carbon atoms, cycloalkylene of 3 to 8 carbon atoms, alkenylene of 2 to 20 carbon atoms, arenylene, aralkylene or cycloalkylalkylene; and each of $R^x$ and $R^y$ when taken independently of each other is (a) hydrogen, (b) an alkyl group of 1 to 20 carbon atoms or an alkenyl group of 2 to 8 carbon atoms, unsubstituted or substituted with cycloalkyl of 3 to 7 carbon atoms, halo, carboxy, alkoxycarbonyl, of 1 to 6 carbon atoms in the alkoxy group, carbamyl, aryl, hydroxy, alkanoyloxy of 1 to 6 carbon atoms, amino, alkylamino of 1 to 6 carbon atoms or dialkylamino of 1 to 6 carbon atoms in each alkyl group; (c) cycloalkyl of 3 to 7 carbon atoms unsubstituted or substituted with alkyl of 1 to 6 carbon atoms; or (d) aryl; or $R^x$ and $R^y$ together with the nitrogen atom to which they are attached are pyrrolidino, piperidino or morpholino.

2. A compound according to claim 1 wherein Y is

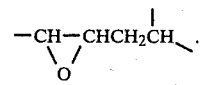

3. A compound according to claim 1 wherein Z is alkylene of 1 to 10 carbon atoms, cycloalkylene of 4 to 6 carbon atoms or phenylmethylene.

4. A compound according to claim 1 wherein each of $R^x$ and $R^y$ independent of the other is hydrogen or alkyl of 1 to 5 carbon atoms.

5. A compound according to claim 1 which is 3-sulphamoyl propyl monate A.

6. A compound according to claim 1 which is 6-sulphamoyl hexyl monate A.

7. A compound according to claim 1 which is 8-sulphamoyl octyl monate A.

8. A compound according to claim 1 which is 3-N,N-dimethyl sulphamoyl propyl monate A.

9. A compound according to claim 1 which is 7-sulphamoyl heptyl-2-yl monate A.

10. A pharmaceutical composition comprising an antibacterially efective amount of a compound according to claim 1 in combination with a pharmaceutically acceptable carrier.

11. A veterinary premix comprising an amount of a compound according to claim 1 sufficient upon dilution at a predetermined ratio with feedstuff or with drinking water to provide upon normal consumption of said feedstuff or drinking water an antibacterially effective amount of said compound, and a veterinarily acceptable carrier.

12. The method for treating bacterial infections in humans and other animals in need thereof which comprises administering thereto an effective amount of a compound according to claim 1.

* * * * *